(12) United States Patent
Dvorsky et al.

(10) Patent No.: US 7,047,058 B1
(45) Date of Patent: May 16, 2006

(54) APPARATUSES, SYSTEMS AND METHODS FOR EXTRAVASATION DETECTION

(75) Inventors: James E. Dvorsky, Hilliard, OH (US); Chad E. Bouton, Delaware, OH (US); Alan D. Hirschman, Glenshaw, PA (US)

(73) Assignee: MEDRAD, Inc., Indianola, PA (US)

( * ) Notice: Subject to any disclaimer, the term of this patent is extended or adjusted under 35 U.S.C. 154(b) by 218 days.

(21) Appl. No.: 10/060,561

(22) Filed: Jan. 30, 2002

Related U.S. Application Data

(60) Provisional application No. 60/266,710, filed on Feb. 6, 2001.

(51) Int. Cl.
*A61B 6/00* (2006.01)

(52) U.S. Cl. ............... 600/407; 600/431; 600/437; 600/438; 600/458; 604/65; 604/66

(58) Field of Classification Search ............ 600/407, 600/300, 437, 431, 458, 438; 128/897, 898, 128/DIG. 13; 604/503, 65, 66
See application file for complete search history.

(56) References Cited

U.S. PATENT DOCUMENTS

| | | |
|---|---|---|
| 3,779,079 A | 12/1973 | Snook |
| 3,951,136 A | 4/1976 | Wall |
| 4,010,749 A | 3/1977 | Shaw |
| 4,240,445 A | 12/1980 | Iskander et al. |
| 4,329,689 A | 5/1982 | Yee |
| 4,378,808 A | 4/1983 | Lichtenstein |
| 4,488,559 A | 12/1984 | Iskander |
| 4,572,182 A | 2/1986 | Royse |
| 4,575,705 A | 3/1986 | Gotcher |
| 4,641,659 A | 2/1987 | Sepponen |
| 4,647,281 A | 3/1987 | Carr |
| 4,648,869 A | 3/1987 | Bobo, Jr. |
| 4,653,501 A | 3/1987 | Cartmell et al. |
| 4,667,679 A | 5/1987 | Sahota |
| 4,690,149 A | 9/1987 | Ko |
| 4,816,019 A | 3/1989 | Kamen |
| 4,819,648 A | 4/1989 | Ko |
| 4,877,034 A * | 10/1989 | Atkins et al. ............. 600/475 |
| 4,923,442 A * | 5/1990 | Segall et al. ............. 604/522 |
| 4,959,050 A | 9/1990 | Bobo, Jr. |
| 4,971,068 A | 11/1990 | Sahi |
| 5,001,436 A | 3/1991 | Scot et al. |

(Continued)

FOREIGN PATENT DOCUMENTS

DE          4007587          9/1991

(Continued)

OTHER PUBLICATIONS

Carr, K. L., "Use of Gallium Arsenide in Medical Applications," IEEE Gallium Arsenide Integrated Circuits (GAAS IC) Symposium, vol. SYMP 17, pp. 10-13, New York (Oct. 29, 1995).

(Continued)

*Primary Examiner*—Ruth S. Smith
(74) *Attorney, Agent, or Firm*—Gregory L. Bradley; Henry E. Bartony, Jr.

(57) ABSTRACT

An apparatus for the detection of extravasation in an imaging procedure includes at least a first source of energy to supply imaging energy to tissue in the vicinity of a site and at least a first sensor to measure a signal resulting from the energy supplied to the tissue by the first imaging energy source. In preferred embodiment, the energy may be one of X-ray, gamma ray or ultrasound energy.

27 Claims, 2 Drawing Sheets

U.S. PATENT DOCUMENTS

| | | | |
|---|---|---|---|
| 5,026,348 A | | 6/1991 | Venegas |
| 5,255,683 A | * | 10/1993 | Monaghan .................. 600/458 |
| 5,334,141 A | | 8/1994 | Carr et al. |
| 5,466,438 A | * | 11/1995 | Unger et al. ............. 424/9.365 |
| 5,628,322 A | * | 5/1997 | Mine ......................... 600/453 |
| 5,769,784 A | | 6/1998 | Barnett et al. |
| 5,840,026 A | * | 11/1998 | Uber et al. .................. 600/431 |
| 5,861,019 A | | 1/1999 | Sun et al. |
| 5,947,910 A | | 9/1999 | Zimmet |
| 5,954,668 A | * | 9/1999 | Uber et al. .................. 600/549 |
| 5,957,950 A | * | 9/1999 | Mockros et al. ............ 606/194 |
| 5,964,703 A | | 10/1999 | Goodman et al. |
| 5,995,863 A | | 11/1999 | Farace et al. |
| 6,026,173 A | | 2/2000 | Svenson et al. |
| 6,061,589 A | | 5/2000 | Bridges et al. |
| 6,233,479 B1 | | 5/2001 | Haddad et al. |
| 6,332,087 B1 | | 12/2001 | Svenson et al. |
| 6,375,624 B1 | | 4/2002 | Uber, III et al. |
| 6,408,204 B1 | | 6/2002 | Hirschman |
| 6,425,878 B1 | | 7/2002 | Shekalim |
| 6,459,931 B1 | | 10/2002 | Hirschman |
| 2002/0040193 A1 | | 4/2002 | Hirschman |
| 2002/0172323 A1 | * | 11/2002 | Karellas et al. ............... 378/51 |
| 2003/0004433 A1 | | 1/2003 | Hirschman |
| 2003/0036674 A1 | | 2/2003 | Bouton |
| 2003/0036713 A1 | | 2/2003 | Bouton et al. |

FOREIGN PATENT DOCUMENTS

| | | |
|---|---|---|
| GB | 2251080 | 6/1992 |
| JP | 11-57001 | 3/1999 |
| WO | WO 99/26685 | 6/1999 |
| WO | WO 99/26686 | 6/1999 |
| WO | WO 99/29356 | 6/1999 |
| WO | WO 01/08729 | 2/2001 |
| WO | WO 03/00972 | 2/2003 |
| WO | WO 03/009753 | 2/2003 |

OTHER PUBLICATIONS

Shaeffer, J. et al., "Early Detection of Extravasation of Radiographic Contrast Medium," Radiology, vol. 184, No. 1, pp. 141-144 (Jul. 1992).

Shaeffer, J., "Detection of Extravasation of Antineoplastic Drugs by Microwave Radiometry," Cancer Letters, 31, pp. 185-291 (1986).

"MMIC Receiver for Water-Vapor Radiometer," NASA Tech. Briefs, 34, (Sep. 1993).

Arkin et al., "Recent Developments in Modeling Heat Transfer in Blood Perfused Tissues," IEEE Transactions on Biomedical Engineering, vol. 41, No., 2, pp. 97-107 (Feb. 1994).

Harris and Von Maltzahn,"Infusion Line Model for the Detection of Infiltration Extravasation and Other Fluid Flow Faults," IEEE Transactions on Biomedical Engineering, vol. 40, No. 2, pp. 154-162 (Feb. 1993).

Montreuil and Nachman, "Multiangle Method for Temperature Measurement of Biological Tissues by Microwave Radiometry," IEEE Transactions on Microwave Theory and Techniques, vol. 39, No. 7, pp. 1235-1238 (Jul. 1991).

Lin, J. C. et al., "Microwave Imaging of Cerebral Edema," Proceedings of the IEEE, vol. 70, No. 5, pp. 523-524 (May 1982).

Kramer, G. G. et al., "Dielectric Measurement of Cerebral Water Content Using a Network Analyzer," Neurological Research, vol. 14, No. 3, pp. 255-258 (Sep. 1992).

Ling, Geoffrey S. F. et al., "Diagnosis of Subdural and Intraparenchymal Intracranial Hemorrhage Using a Microwave Based Detector," Digitization of the Battlespace V and Battlefield Biomedical Technologies II, vol. 4037, pp. 212-217 (Apr. 24, 2000).

Behari, J., et al., "Dielectric Permittivity of Biological Tissues in the Microwave Frequency Range," Proceedings of the SPIE-The International Society for Optical Engineering, Advanced Microwave and Millimeter-Wave Detectors, vol. 2275, pp. 301-308, San Diego, CA (Jul. 25-26, 1994).

International Search Report for Counterpart PCT Application PCT/US00/20112.

International Search Report for Counterpart PCT Application PCT/US02/23925.

Andreuccetti, D., et al. "High Permittivity Patch Radiator for Single and Multi-Element Hyperthermia Applicators," IEEE Transactions on Biomedical Engineering, vol. 40, No. 7, pp. 711-715, IEEE Inc., New York (Jul. 1, 1993).

International Search Report for PCT Application No. PCT/US02/23877.

Lee, E. R., et al., "Body Conformable 915 MHz Microstrip Array Applicators for Large Surface Area Hyperthermia," IEEE Transactions on Biomedical Engineering, vol. 39, No. 5, pp. 470-483, IEEE Inc., New York (May 1, 1992).

* cited by examiner

APPARATUSES, SYSTEMS AND METHODS FOR EXTRAVASATION DETECTION

CROSS-REFERENCE TO RELATED APPLICATION

This application claims priority to U.S. Provisional Application Ser. No. 60/266,710, filed on Feb. 6, 2001.

BACKGROUND OF THE INVENTION

The present invention relates generally to the detection of extravasation of fluids injected into a patient, and, more particularly, to extravasation detection apparatuses, systems and methods in medical injection procedures using energy transmission through tissue in the vicinity of an injection site or other site.

In many medical diagnostic and therapeutic procedures, a physician or other person injects a patient with a fluid. In recent years, a number of injector-actuated syringes and powered injectors for pressurized injection of contrast medium in procedures such as angiography, computed tomography, ultrasound and NMR/MRI have been developed.

Extravasation is the accidental infusion of an injection fluid such as a contrast medium into tissue surrounding a blood vessel rather than into the blood vessel itself. Extravasation can be caused, for example, by fragile vasculature, valve disease, inappropriate needle placement, or patient movement resulting in the infusing needle being pulled from the intended vessel or causing the needle to be pushed through the wall of the vessel. Furthermore, high injection pressures and/or rates of some modern procedures increase the risk of extravasation. In computed tomography, for example, contrast injection flow rates can be in the range of 0.1 to 10 ml/s.

Moreover, extravasation can cause serious injury to patients. In that regard, certain injection fluids such as contrast media or chemotherapy drugs can be toxic to tissue if not diluted by blood flow. It is, therefore, very important when performing fluid injections to detect extravasation as soon as possible and discontinue the injection upon detection.

Several extravasation techniques are known in the art. Two simple and very useful techniques for detecting extravasation are palpation of the patient in the vicinity of the injection site and simple visual observation of the vicinity of the injection site by a trained health care provider. In the palpation technique, the health care provider manually senses swelling of tissue near the injection resulting from extravasation. By visual observation, it is also sometimes possible to observe directly any swelling of the skin in the vicinity of an injection site resulting from extravasation.

In addition to palpation and observation, there are a number of automated methods of detecting extravasation that may include automatic triggering of an alarm condition upon detection. Unfortunately, each of these automated methods of detecting extravasation is limited by significant drawbacks.

U.S. Pat. No. 4,647,281, for example, discloses subcutaneous temperature sensing of extravasation to trigger an alarm. In this method of extravasation detection, an antenna and a microwave radiometer instantaneously measure the temperature of the subcutaneous tissue at the site where fluid is injected. An algorithm periodically determines the temperature difference between the tissue and the injected fluid, and compares the difference to a fixed threshold. An alarm processor uses the comparison to determine an alarm condition.

In addition, U.S. Pat. No. 5,334,141 discloses a microwave extravasation detection system employing a reusable microwave antenna and a disposable attachment element for releasably securing the microwave antenna to a patient's skin over an injection site. The attachment element holds the antenna in intimate contact with the patient's skin to optimize microwave transfer therebetween, while shielding the antenna from environmental noise signals. Although measurement of temperature changes and emissivity using microwave energy can result in instantaneous detection, temperature differences are often too small for practical measurement.

Several plethysmographic detection techniques are available in addition to known temperature sensing techniques. For example, mercury strain gauge plethysmographs measure the volume change resulting from venous blood flow in a cross-sectional area of a limb of a patient. Air cuff or pulse volume recorder plethysmographs measure the changes in pressure within a recording cuff caused by the change in volume of a limb or digit as a result of extravasation. Such plethysmographs can be cumbersome to operate and/or insensitive to small changes in volume.

Photo-plethysmographs measure the optical scattering properties of capillary blood to detect the presence of extravasated fluids in tissue. An example of a photo-plethysmograph is described in U.S. Pat. No. 4,877,034. Because light is heavily absorbed in tissue, however, the sensitivity of photo-plethysmographs is generally limited to the top ¼ inch to ½ inch of tissue. Most extravasations, however, occur deeper than ¼ inch to ½ inch. Moreover, the injection medium may flow into interstitial spaces remote from the photo-plethysmograph sensors and go undetected.

Impedance plethysmographs measure changes in the electrical impedance in a defined tissue volume of a limb. In this method, an impedance change of a certain level in the vicinity of the injection site is interpreted as being an extravasation. A change in impedance occurs during extravasation because injection fluid in the tissue of the patient changes both the volume and the electrical impedance properties of the tissue. Use of electrodes in impedance plethysmographs can, however, result in instabilities. For example, maintaining suitable electrical contact between the electrodes of impedance plethysmographs and the skin of the patient is often very difficult.

It is, therefore, very desirable to develop improved devices and methods for detecting extravasation during, for example, the high flow rate procedures (1 to 10 ml/sec) typically encountered in angiographic, CT, ultrasound, and MR imaging procedures.

SUMMARY OF THE INVENTION

Current automated methods for detecting extravasation do not take adequate advantage of the inherent or designed properties of the injection fluid. In the case of a contrast medium, for example, the contrast medium is designed to affect a certain type or types of applied energy (that is, the imaging energy) to provide an enhanced image of an internal region (sometimes referred to as a region of interest or ROI) of a patient. The inherent or designed properties of an injection medium can be used to provide a sensitive measurement of extravasation in real time.

In one embodiment, the present invention provides an apparatus for the detection of extravasation in an imaging procedure. Such imaging procedures typically include the steps of injecting a contrast medium into a patient and supplying imaging energy from a first source of imaging energy to a region of interest of the patient to create an image of the region of interest. As discussed above, this image is enhanced by the effect the contrast medium has upon the imaging energy in the region of interest. In general, the extravasation detection apparatus includes at least a second source of imaging energy to supply imaging energy to tissue in the vicinity of a site. The apparatus also includes at least one sensor to measure a signal resulting from the imaging energy supplied to the tissue by the second imaging energy source.

The apparatus of the present invention thus uses the inherent or designed properties of the contrast medium to detect extravasation of the contrast medium. For example, in the case of a contrast medium designed to be use in connection with a procedure in which X-rays are used as the imaging energy (for example, computed tomography or CT), the contrast medium is designed to absorb, block or scatter transmission of X-rays and low energy gamma rays. In this embodiment, a source of X-rays or gamma rays preferably provides a safely low level of such energy to a site on a patient's limb at which extravasation is to be detected (for example, the injection site). An energy sensor or detector that is suitable for detecting X-rays and/or gamma rays is preferably positioned on an opposing side of the limb from the energy source. The level of energy detected by the sensor provides an instantaneous and sensitive measurement of extravasation.

Other energy sources can be used in the present invention depending upon the properties of the contrast medium. Ultrasound imaging, for example, creates images of the human body by broadcasting ultrasonic energy into the body and analyzing the reflected ultrasound energy. Differences in reflected energy (for example, amplitude or frequency) appear as differences in gray scale or color on the output images. As with other medical imaging procedures, contrast media can be injected into the body to increase the difference in the reflected energy and thereby increase the gray scale or color contrast displayed in the image (that is, the image contrast) viewed by the operator. These same properties of an ultrasound contrast medium used to enhance the imaging procedure can also be used to detect extravasation.

Preferably, the second imaging energy source and the sensor are positioned in a manner so that the vicinity of the site is available for palpation and visible for visual inspection. Unlike many other devices for automated detection of extravasation, the energy source(s) and the sensor(s) of the present invention need not be in contact with patient.

It is not necessary that the energy source used in the extravasation detection apparatus of the present invention deliver the same type of energy that is delivered to the region of interest to produce an enhanced image. Indeed, the extravasation detection apparatuses of the present invention are not limited to imaging procedures and can be used in any injection procedure in which there is a potential for extravasation. For example, any injection medium that will reflect, scatter and/or absorb a type of energy can be detected by the extravasation detection apparatuses of the present invention. In general, the presence of such injection media will change the strength of an energy signal that is supplied thereto. For example, any injection medium that contains heavy metal ions is capable of absorbing or scattering X-rays or low energy gamma rays. Such injection media are, for example, used as contrast media in magnetic resonance imaging as well as in CT.

The present invention thus provides a method of detecting extravasation of an injection medium including the steps of supplying energy to tissue in the vicinity of a site and measuring a resultant signal. The energy is preferably selected so that the injection medium will reflect, scatter and/or absorb the energy. Moreover, the energy is preferably chosen to penetrate beyond superficial tissue layers (for example, to a depth greater than ½ inch).

In the case of an injection medium that does not inherently reflect, scatter and/or absorb energy, an additive can be placed in the injection medium to act as an extravasation detection medium. For example, an ultrasound contrast agent can be added to a chemotherapy agent for detection using ultrasonic energy. The present invention thus further provides a method for detecting extravasation in an injection procedure in which an injection medium is injected into a patient that includes the steps of: mixing an additive with the injection medium; supplying energy to tissue in the vicinity of a site; and measuring a signal resulting from the energy supplied to the tissue. The additive is adapted to affect the signal so that extravasation is detectable.

The present invention further provides an injection system including a powered injector and an extravasation detection apparatus. The extravasation detection apparatus includes at least one source of energy to supply energy to tissue in the vicinity of a site and at least one sensor to measure a resultant signal. In general, the signal is proportionate to the energy reflected, scattered and/or absorbed by extravasated fluid in the vicinity of the site.

The present invention also provides an apparatus for the detection of extravasation including at least a first source of X-ray energy or gamma ray energy to supply X-ray energy or gamma ray energy and at least a first sensor to measure a signal resulting from the energy supplied to the tissue. Likewise, the present invention also provides an apparatus for the detection of extravasation including at least a first source of ultrasonic energy to supply ultrasonic energy and at least a first sensor to measure a signal resulting from the ultrasonic energy supplied to the tissue.

The present invention also provides a method for detecting extravasation in an imaging procedure. As discussed above, the imaging procedure generally includes the steps of injecting a contrast medium into a patient and supplying imaging energy to a region of interest of the patient to enhance an image. The method of the present invention includes the steps of: supplying imaging energy to tissue in the vicinity of a site; and measuring a signal resulting from the imaging energy supplied to the tissue.

Likewise, the present invention provides a method for detecting extravasation including the steps of (1) supplying X-ray energy, gamma ray energy and/or ultrasonic energy to tissue in the vicinity of a site, and (2) measuring a signal resulting from the energy supplied to the tissue.

In some patients, extravasation sometimes occurs at a site remote from the catheter insertion point (that is, the injection site). The present invention easily affords the ability to detect extravasation at the injection site and/or any position or site remote from an injection site, but along a path of potential extravasation. Multiple energy sources and/or multiple sensors may be positioned along a path of potential extravasation.

Numerous other advantages are afforded by the apparatuses, systems and methods of the present invention as compared to current apparatuses, systems and methods of detecting extravasation. For example, a larger portion of tissue can be probed for the presence of extravasated injection fluid.

Unlike prior modalities, detection of extravasation in the present invention is not sensitive only in superficial layers of tissue, but can preferably reach through the entire tissue volume into which injection fluid can migrate in the case of extravasation.

Moreover, because contact with the patient is not required in the present invention, the detection site(s) remain open for visualization and/or palpation. Likewise, tight coupling of transducers to the patient's skin and attendant discomfort and/or tissue damage are avoided. The devices of the present invention can also be used in connection with multiple procedures and patients, eliminating the expense and operative inconvenience associated with disposable sensors used in other techniques.

The present invention and its attendant advantages will be further understood by reference to the following detailed description and the accompanying drawings.

DETAILED DESCRIPTION OF THE INVENTION

Figure 1:
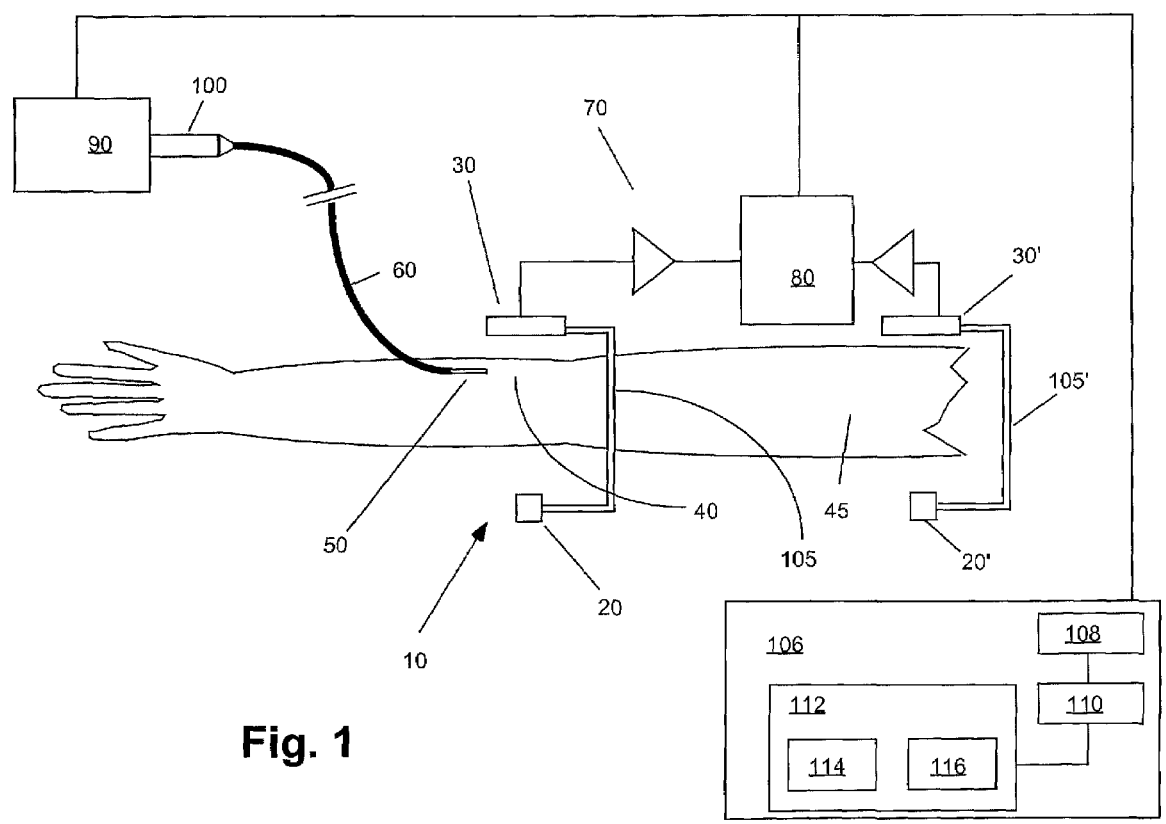
FIG. 1 illustrates a side view of an embodiment of a device or apparatus for detecting extravasation of the present invention.

FIG. 1 illustrates one embodiment of an extravasation detection apparatus or device 10 of the present invention. Extravasation detection device 10 preferably includes an energy source 20 that is preferably positioned on one side of a site at which extravasation is to be detected. A sensor 30 suitable to detect a signal resulting from transmission of the energy emitted by energy source 20 may be positioned opposite energy source 20 such that energy (for example, X-ray energy or gamma ray energy) that is emitted by energy source 20 and is transmitted through the tissue of a patient's limb 45 is detected by sensor 30.

In the case that reflected energy is to be measured (for example, in the case of ultrasound energy), energy source 20 and sensor 30 are preferably positioned on the same side of a site. In FIG. 1, energy source 20 and sensor 30 are positioned about an injection site 40 on a patient's limb 45 as defined by injection needle 50, which is connected to a source of injection fluid by a fluid path 60.

During an injection procedure, energy emitted by energy source 20 supplies energy to the tissue of limb 45, and a resultant signal is detected by sensor 30. Unlike prior extravasation detection systems, inherent or designed properties of the injection fluid may be used in the apparatus of the present invention to detect extravasation. For example, injection fluids such as contrast media used in imaging procedures are chosen or designed to respond in a particular manner to imaging energy. For example, the imaging energy may be transformed, reflected, scattered and/or absorbed by a contrast medium. It is this property of a contrast medium that enables enhancement of an image of a region of interest. These and other inherent properties of an injection medium (or an additive thereto) can be used to provide a sensitive detection of extravasation in real time.

Sensor 30 is preferably connected via circuitry 70 (as known in the art) to an alarm device 80 to provide an indication (for example, an audible, visible or tactile indication) to an operator that extravasation is occurring. Circuitry 70 can also be in communicative connection with a powered injector 90 used to pressurize injection fluid contained within a syringe 100 that is in fluid connection with fluid path 60. Detection of extravasation can, for example, result in automatic cessation of the injection procedure by injector 90.

Extravasation device 10 can also be in communicative connection with an imaging system 106. Imaging system 106 may, for example, comprise a source of imaging energy 108 and a signal receiver 110. Receiver 110 is preferably in communicative connection with an imager 112 that may, for example, comprise a processing unit 114 and a display 116. Warning of extravasation can, for example, be displayed on display 116. A record of the occurrence of extravasation can also be maintained on a memory unit of processing unit 114 or another computer system.

Preferably, a fixed geometry is maintained between source 20, sensor 30 and site 40 to ensure consistent measurement. Source 20 and sensor 30 may, for example, be connected in a fixed relationship to each other by a frame 105 that can be positioned in a fixed manner relative to site 40.

Extravasation typically occurs in the immediate vicinity of the injection site. Extravasation may sometimes occur, however, at a site remote from the injection site 40. In the embodiment of FIG. 1, extravasation can be detected at a site remote from an injection site (but along a path of potential extravasation) using a second energy source 20' and a second sensor 30' that are preferably connected by a frame member 105'. Source 20' and sensor 30' operate as described above in connection with source 20 and sensor 30. Multiple energy source/sensor couplings of the present invention can be positioned as an array along a path of potential extravasation. It is thus possible to detect extravasation that may occur at remote locations as a result of injection of the fluid into the patient at the injection site.

Figure 2:
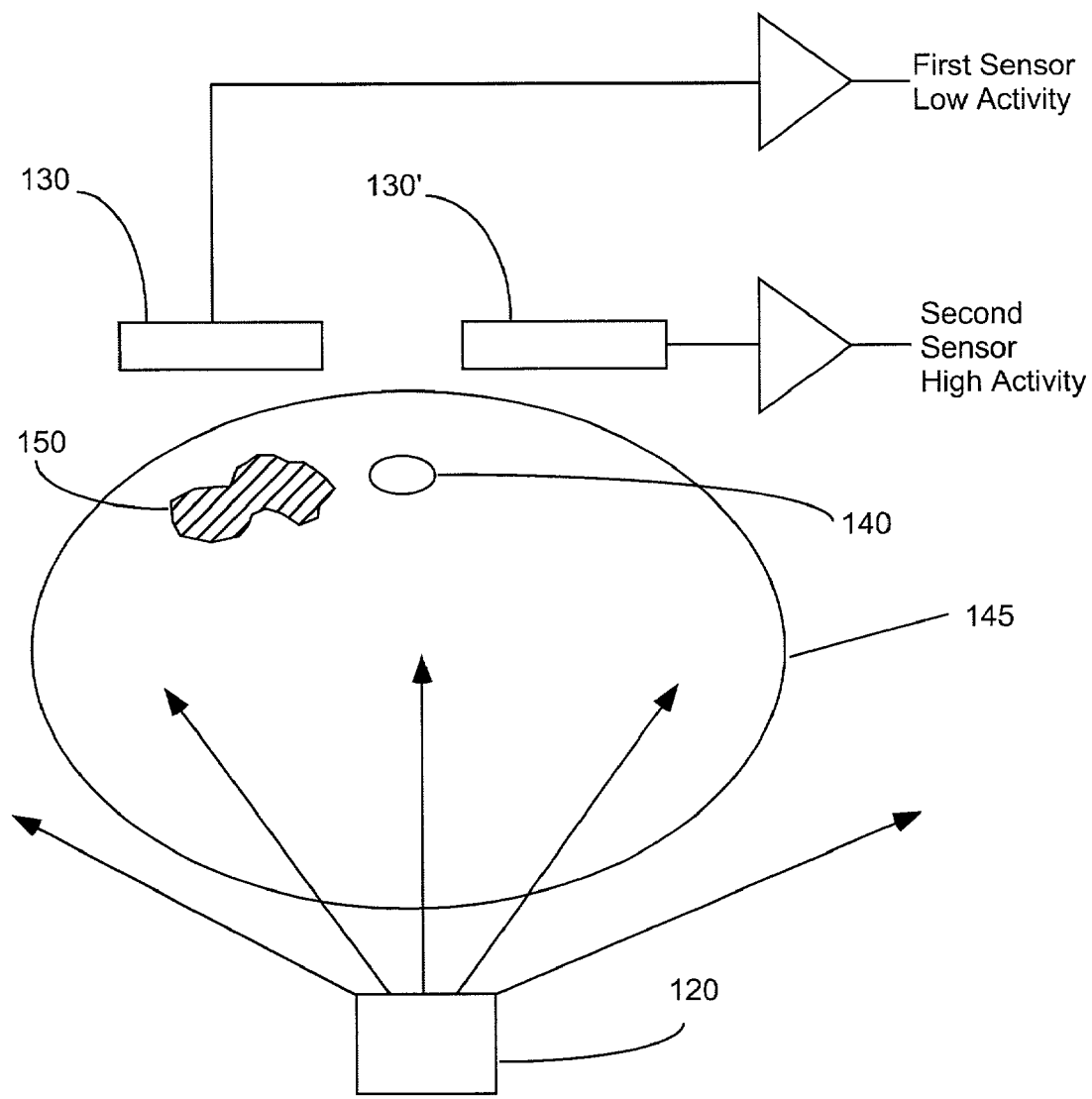
FIG. 2 illustrates another embodiment of a device or apparatus for detecting extravasation of the present invention.

The operation of one embodiment of the present invention will be discussed in further detail with reference to FIG. 2. In FIG. 2, a source 120 of, for example, low-level gamma rays (represented by arrows) is positioned opposite from sensors 130 and 130', each of which preferably includes a high-energy photonic detector. A patient's limb 145 is positioned between source 120 and sensors 130 and 130', which are positioned on each side of an artery 140.

Gamma ray source 120 can, for example, be any number of long half-life radioisotopes, such as Iodine-129 or Americium-241. Sensors 130 and 130' can, for example, include a photo multiplier tube, a solid-state detector (such as a cadmium-zinc-telluride or equivalent detector), or another gamma ray detector as known in the art.

Under conditions of no extravasation (as represented by the area on the right side of artery 140 in FIG. 2), gamma rays emitted from source 120 will pass through the limb and strike sensor 130'. Sensor 130' will register those gamma rays. Intervening tissue offers some resistance to the migration of high-energy photons, but this resistance is limited compared to the effect of the presence of contrast medium. Preferably, a baseline measurement is made before an injection procedure begins to account for the effect of intervening tissue on the energy. In the absence of extravasation, sensor 130' will register high activity (that is, generally equivalent to the baseline measurement).

When extravasation occurs, as represented by area to the left side of artery 140 in FIG. 2, contrast medium 150 "blocks" photons from striking sensor 130. Sensor 130 will, therefore, register measurably lower activity than the baseline measurement and an extravasation alarm can be indicated and/or the injection procedure automatically ended. A threshold value of change in activity from a baseline measurement is readily established to determine if extravasation has occurred.

Because contact with the patient's limb is not required in the present invention, the vicinity of the detection site is maintained in an unobstructed state for palpation and/or visual observation by health care providers.

Although the present invention has been described in detail in connection with the above embodiments and/or examples, it is to be understood that such detail is solely for that purpose and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:

1. An apparatus for the detection of extravasation, comprising:
   at least a first energy source adapted to supply X-ray energy or gamma ray energy to tissue in the vicinity of a site along a path of potential extravasation of fluid from a blood vessel into which fluid is injected;
   at least a first sensor to measure a signal resulting from the energy supplied to the tissue by the first energy source, the signal being proportional to the X-ray energy or gamma ray energy transformed, reflected, scattered or absorbed by an extravasated fluid present in the vicinity of the site; and
   an indicator to provide an indication of the occurrence of extravasation.

2. The apparatus of claim 1 wherein the at least a first energy source and the at least a first sensor are connected by a frame member to fix the geometry of the at least a first energy source and the at least a first sensor about the site so the X-ray energy from the at least a first energy source passes through tissue in the vicinity of the site to the at least a first sensor.

3. The apparatus of claim 1 wherein the indicator comprises an alarm to indicate the occurrence of extravasation.

4. The apparatus of claim 3 wherein an alarm is indicated if the energy measured at the at least a first sensor falls below a threshold value.

5. The apparatus of claim 1 wherein the first energy source and the first sensor do not contact the skin of a patient.

6. The apparatus of claim 1 wherein the first energy source and the first sensor are positioned in a manner so that the vicinity of an injection site is available for palpation and visible for visual inspection.

7. An apparatus for the detection of extravasation, comprising:
   at least a first energy source adapted to supply ultrasonic energy to tissue in the vicinity of a site along a path of potential extravasation of fluid from a blood vessel into which fluid is injected;
   at least a first sensor to measure a signal resulting from the energy supplied to the tissue by the first energy source, the signal being proportional to the ultrasonic energy reflected, scattered or absorbed by an extravasated fluid present in the vicinity of the site; and
   an indicator to provide an indication of the occurrence of extravasation.

8. The apparatus of claim 7, wherein the indicator comprises an alarm system to indicate the occurrence of extravasation.

9. The apparatus of claim 8 wherein the occurrence of extravasation is determined by comparing the energy measured at the at least a first sensor to a threshold value.

10. The apparatus of claim 7 wherein the first energy source and the first sensor do not contact the skin of a patient.

11. The apparatus of claim 7 wherein the first energy source and the first sensor are positioned in a manner so that the vicinity of an injection site is available for palpation and visible for visual inspection.

12. A method for detecting extravasation in an injection procedure, comprising:
   supplying at least one of X-ray energy, gamma ray energy or ultrasonic energy to tissue in the vicinity of a site along a path of potential extravasation of fluid from a blood vessel into which fluid is injected;
   measuring a signal resulting from the energy supplied to the tissue, the measured signal being proportional to the X-ray energy, gamma ray energy or ultrasonic energy transformed, reflected, scattered or absorbed by an extravasated fluid present in the vicinity of the site; and
   analyzing the measured signal to determine whether an extravasated fluid is present in the vicinity of the site.

13. The method of claim 12, further comprising:
   measuring a baseline signal before beginning the injection procedure.

14. The method of claim 13, further comprising:
   comparing the measured signal to the baseline signal to determine whether an extravasated fluid is present in the vicinity of the site.

15. An injection system comprising:
   a powered injector; and
   an extravasation detection apparatus comprising:
      at least one source of energy to supply at least one of x-ray energy, gamma ray energy, or ultrasonic energy to tissue in the vicinity of a site along a path of potential extravasation of fluid from a blood vessel into which fluid is injected;
      at least one sensor to measure a signal resulting from the energy supplied to the tissue in the vicinity of the site, the signal being proportional to the x-ray energy, gamma ray energy or ultrasonic energy transformed, reflected, scattered or absorbed by an extravasated fluid present in the vicinity of the site; and
      an indicator to provide an indication of the occurrence of extravasation.

16. The apparatus of claim 15, wherein the indicator comprises an alarm in communication with the extravasation detection apparatus to indicate occurrence of extravasation.

17. The apparatus of claim 16 wherein the alarm indicates extravasation based upon comparing the signal to a threshold value.

18. The apparatus of claim 15 wherein the injector and the extravasation detection apparatus are in communicative connection so that an injection procedure is stopped by the injector upon detection of extravasation.

19. The injection system of claim 15 wherein the energy source and the sensor do not contact the skin of a patient.

20. The injection system of claim 15 wherein the energy source and the sensor are positioned in a manner so that the vicinity of an injection site is available for palpation and visible for visual inspection.

21. A method for detecting extravasation in an injection procedure, comprising:
   supplying x-ray energy, gamma ray energy or ultrasonic energy to tissue in the vicinity of an injection site along a path of potential fluid extravasation from a blood vessel into which contrast medium is injected;

measuring a baseline signal resulting from the energy supplied to the tissue;

mixing an additive with a contrast medium;

injecting the contrast medium containing the additive through the injection site into the blood vessel;

supplying x-ray energy, gamma ray energy or ultrasonic energy to tissue in the vicinity of the injection site;

measuring a signal resulting from the energy supplied to the tissue, the measured signal being proportional to the X-ray energy, gamma ray energy or ultrasonic energy transformed, reflected, scattered or absorbed by extravasated contrast medium containing the additive present in the vicinity of the site, the additive being adapted to affect the signal;

detecting whether an extravasation has occurred by comparing the measured signal to the baseline signal to determine whether extravasated contrast medium containing the additive is present in the vicinity of the site; and indicating that an extravasation has occurred.

22. A method of detecting extravasation of an injection medium, comprising:

supplying x-ray energy, gamma ray energy or ultrasonic energy to tissue in the vicinity of a site along a path of potential extravasation of fluid from a blood vessel into which injection medium is injected, the energy being selected so that the injection medium will reflect, scatter or absorb the energy;

measuring a signal proportional to the amount of energy reflected, scattered or absorbed;

detecting whether an extravasation has occurred by analyzing the measured signal to determine whether extravasated medium is present in the vicinity of the site; and indicating that an extravasation has occurred.

23. The method of claim 22, further comprising:

measuring a baseline signal corresponding to a situation in which there is no extravasation.

24. The method of claim 23, further comprising:

comparing the measured signal to the baseline signal to determine whether an extravasated fluid is present in the vicinity of the site.

25. An injection system for delivering fluid to a patient during an injection procedure, the injection system comprising:

an injector; and an extravasation detection system in communication with the injector, the extravasation detection system comprising:

an energy source adapted to supply at least one of x-ray energy, gamma ray energy, or ultrasonic energy to tissue of the patient in the vicinity of a fluid injection site;

a sensor adapted to measure a signal resulting from the energy supplied to the tissue in the vicinity of the fluid injection site, the signal being proportional to the x-ray energy, gamma ray energy or ultrasonic energy transformed reflected, scattered or absorbed by an extravasated fluid present in the vicinity of the fluid injection site; and an alarm to provide an indication of the occurrence of extravasation;

wherein the alarm is activated when an extravasated fluid is detected by the extravasation detection system.

26. A method for detecting extravasation during a fluid injection procedure, comprising;

supplying x-ray energy, gamma ray energy or ultrasonic energy to tissue in the vicinity of a proposed fluid injection site;

measuring a baseline signal resulting from the energy supplied to the tissue;

commencing the fluid injection procedure;

supplying x-ray energy, gamma ray energy or ultrasonic energy to tissue in the vicinity of the fluid injection site;

measuring a signal resulting from the energy supplied to the tissue, the measured signal being proportional to the X-ray energy, gamma ray energy or ultrasonic energy transformed, reflected, scattered or absorbed by an extravasated fluid present in the vicinity of the site; and comparing the measured signal to the baseline signal to determine whether an extravasated fluid is present in the vicinity of the site.

27. The method of claim 26, further comprising:

terminating the injection procedure if an extravasated fluid is present.

* * * * *